(12) United States Patent
Cherif-Cheikh et al.

(10) Patent No.: US 6,902,543 B1
(45) Date of Patent: Jun. 7, 2005

(54) DEVICE FOR RECONSTITUTING A THERAPEUTIC SOLUTION, SUSPENSION OR DISPERSION

(75) Inventors: Roland Cherif-Cheikh, Castelldefels (ES); Christophe Aubert, Cudrefin (CH)

(73) Assignee: Societe de Conseils de Recherches et Applications Scientifiques (S.C.R.A.S.) (FR)

( * ) Notice: Subject to any disclaimer, the term of this patent is extended or adjusted under 35 U.S.C. 154(b) by 212 days.

(21) Appl. No.: 10/110,362
(22) PCT Filed: Oct. 10, 2000
(86) PCT No.: PCT/FR00/02804
§ 371 (c)(1), (2), (4) Date: Apr. 16, 2002
(87) PCT Pub. No.: WO01/26718
PCT Pub. Date: Apr. 19, 2001

(30) Foreign Application Priority Data

Oct. 13, 1999 (FR) ............................................ 99 12748

(51) Int. Cl.⁷ ............................................. A61M 37/00
(52) U.S. Cl. ............................ 604/82; 604/87; 604/187
(58) Field of Search ................................ 604/82–93.01, 604/187, 181

(56) References Cited

U.S. PATENT DOCUMENTS

| 4,581,016 A | 4/1986 | Gettig |
| 4,886,495 A | 12/1989 | Reynolds |
| 5,395,325 A | 3/1995 | Moreno et al. |
| 5,569,191 A * | 10/1996 | Meyer ........................ 604/82 |

FOREIGN PATENT DOCUMENTS

| EP | 0298585 | 1/1989 |
| FR | 2604363 | 4/1988 |
| HU | 211712 | 12/1995 |
| HU | 0002580 | 12/2000 |
| WO | 9532015 | 5/1994 |
| WO | WO97/46202 | 12/1997 |

\* cited by examiner

*Primary Examiner*—Kevin C. Sirmons
(74) *Attorney, Agent, or Firm*—Muserlian, Lucas and Mercanti

(57) ABSTRACT

The invention relates to a syringe-type device for freshly preparing a solution, suspension or dispersion, for example injectable formulations, preferably according to a method for reconstitution in a vacuum. The device is shown in FIG. 1. The invention also relates to a method for packing the fresh preparation of the solution, suspension or dispersion in a cylindrical reservoir that can be used in a single or multi-dose syringe provided for the same. This is a method for packing the preparation inside the cylindrical reservoir, which is closed on one side by an injection plunger whose movement in the reservoir is limited. This method is characterised in that the elements to be packed are introduced into the reservoir from the injection plunger side before the reservoir is closed by said plunger. Said reservoir is a tube or ampule which is closed on the other side in advance.

9 Claims, 11 Drawing Sheets

DEVICE FOR RECONSTITUTING A THERAPEUTIC SOLUTION, SUSPENSION OR DISPERSION

A subject of the present invention is a device for the extemporaneous preparation of a solution, a suspension or a dispersion, for example injectable formulations preferably according to a vacuum-based reconstitution procedure called VAC ("Vacuum Automatic Control") which is the subject of the previous French Patent Application No. 96/06886. A subject of the present invention is also a preparation and packaging process of said formulations in said devices according to which the reservoir of said devices containing the solid part of said formulation will then be sealed on the piston side, preventing its injection or its release after reconstitution.

According to the invention, the device is preferably used as a device in which a part of the formulation is vacuum-packed and another is constituted by the liquid part of the final preparation, each of them being packed in a separate reservoir forming part of said device.

In therapeutic preparations and, by way of example, more particularly in the case of injectable forms, it is sometimes useful, preferable or even indispensable to separate the constituents. The device and the process which are a subject of the present invention are more particularly useful in the cases in which one part of said constituents is in non-liquid form and another in liquid form. In particular, they can be applied to any lyophilizate of injectable solutions, to a powder or any other vacuum-packed solid forms such that they can form, after reconstitution, a liquid, a gel or an injectable paste-like form.

By way of example of a form illustrating the usefulness of this invention, without this being limitative with regard to other possible applications, we can take the injectable forms in which one part is in dry or solid form and another constitutes the liquid injection vehicle.

More precisely, the solid part will in general contain the active ingredient and can be a lyophilized form and the injection vehicle can be an aqueous preparation intended to hydrate the dry form before injection. The aim is then to reconstitute a solution or a suspension or even an injectable dispersion.

This type of injectable form is widespread and the reasons for which they are used rather than a mixed liquid form are well known.

In particular, problems of stability or compatibility of the constituents in the liquid mixture can be mentioned. Although such a separate solid-liquid packaging allows the improvement of certain points, such as for example the preservation of the formulation over time at a temperature compatible with its transport and storage, the fact remains that it is an arrangement which poses numerous specific problems associated in particular with the existence of two sub-systems.

The traditional solution for this type of preparation is to bottle the solid or lyophilized form, which is hydrated at the time of use by transfer from a syringe injecting the liquid medium by means of a needle inserted through the stopper of the bottle. Once hydrated, the formulation is generally recovered by the same needle in said syringe. This syringe can have been previously loaded with liquid- from an ampoule or a first bottle or the syringe can be pre-filled with the liquid phase of the mixture.

This relatively complicated operation sets the constitutive elements of the formulation in motion several times and presents risks of contamination (or contact with the needle) both for the user and the recipient patient. The variability of the results and therefore of the treatment administered remains not inconsiderable depending on imponderable parameters such as the suitability or practice of the operator.

A certain number of technical solutions for the device have therefore been developed in an attempt to simplify this preparation and/or to reduce the risks.

Certain solutions remain fairly close to the standard procedure starting with packaging in several elements and seeking only to reduce part of the risk or problem. This is in particular the case for technical solutions in which an intermediate element is added between the bottle and the syringe in order to simplify the injection and recovery of the liquid. For example, the Monovial® device from Becton Dickinson or Vial-Mate® from Baxter can be mentioned.

Although this approach hardly simplifies the extemporaneous preparation and is not in the category of pre-filled packagings or syringes, it has the merit above all in the eyes of the pharmaceutical industry of not modifying the primary bottling of the solid form, synonymous with a filling and treatment process which is fully validated and known, using existing equipment.

Of course, there are other more radically novel approaches to the device for simplifying this problem which in general involve a pre-filled packaging or syringe. For example, there may be cited the use of bi-compartmental syringes which are generally equipped with deviations or a by-pass where the mobile separators which exist between the two parts of the same reservoir can be deactivated. By way of example, Becton Dickinson's Hypack liqui-dry® syringes or Vetter's Lyoject® syringe can be mentioned. In this case, the mobile separator is a piston which, at the moment of rehydration, will move vis-a-vis a deviation arranged in the wall of the syringe.

This elegant solution has the advantage of reducing the injectable elements to a single unitary device. In its basic version, this solution can pose risks of error or incorrect handling during the reconstitution operation; however, certain practised improvements can allow these risks to be considerably reduced.

The main drawback for the pharmaceutical industry of such a device remains associated with the packaging in one and the same reservoir of two constituents one of which is liquid and the other solid and which do not usually have at all the same method of treatment and/or sterilization above all when the solid is prepared by lyophilization. Another drawback in this case is associated with the size or volume occupied by the bi-compartmnental element in the lyophilizer which, given the portion of the reservoir then allowed for the liquid part, can be twice as large as in separate reservoirs.

In addition to this, there is the stability risk associated with the proximity and possibility of contact between the two parts of the reservoir through the mobile separator or piston.

Faced with this problem, other approaches to the packaging in a single device have been attempted in which the packaging is, this time, carried out in two truly separate reservoirs.

By way of example, in this regard, the patent application PCT WO 94/13344 (Meyer), can be mentioned, which describes a device in which the solvent or liquid is packed in a cartridge which can be standard and the second part of the formulation (which can be a lyophilizate) is contained in a straight specific tube with a sealed base.

There can also be mentioned Patent Application EP 298,595 which describes a syringe constituted by several interlocking elements including two reservoirs sealed before use, which can be connected via a double-tipped needle.

The pistons called "obturators-pistons-valves" are characteristic and in particular the tube piston which has grooves for a pre-positioning in lyophilization, also synonymous with dead volume.

The device is designed to be fully assembled, which means carrying out this operation in aseptic conditions, or envisaging a joint liquid-solid post-sterilization which risks being incompatible with one of the phases or with the current thrust of certain directives. In this, this device does not resolve the problem of unitary packaging, and therefore treatment, of bi-compartmental devices.

In the light of the very broad industrial development of certain processes for filling around standard reservoirs or containers and the known needs for aseptic preparation or customary post-sterilization, it would be very desirable to be able, in this specific case of formulation in two sub-units, to have available a device which simplifies and secures extemporaneous preparation whilst allowing the use of standard treatments of existing reservoir sub-systems. This requirement preferably involves the use of a prefilled device which avoids problematic transfers. For certain very fragile or sophisticated products, it is important to avoid the agitation and movement created by these transfers.

Another aspect of the problem associated with the operations of mixing the two parts of the formulation then degassing (with risk of contamination depending on the extent and time of contact with the ambient medium) explains the search for devices in which this mixing is simplified and, if possible, effected without prior opening to the outside, even of devices in which degassing could be avoided.

The way in which the reconstitution is carried out and in particular its speed of realization and the losses associated with transfer and degassing remain, whatever the device, random parameters which can lead to dissimilar results.

French patent application no. 96/06886 describes a process according to which this reconstitution becomes automatic after actuation under the action of the vacuum and in which the degassing operation is quite simply omitted.

The applicant has now invented advantageous devices which satisfy all of these desiderata, for example in the form of an "in-syringe" arrangement very close to that commonly known which allows the same therapeutic steps to be preserved and the most standard reservoirs to be used. These devices and these arrangements are characterized in that the non-liquid part of the formulation to be injected is packed in the body of the syringe and the liquid reconstitution part is packed separately in a reservoir which can form the injection rod of the piston of the syringe. These arrangements are realized, in particular starting from standard reservoirs, by applying the preparation and packaging process which constitutes the other part of the invention and which consists of filling and sealing from the rear at the piston.

Similarly, the transfer system between the two parts is provided by a needle, a tube or a rod which has the characteristic of entering the non-liquid reservoir through the piston which will serve for the injection of the reconstituted form.

These devices, according to the invention, moreover offer a means of blocking said injection piston which allows the installation of said transfer system in said piston; said means of blocking can then be deactivated, thus releasing said injection piston.

Finally, the device can include a mechanism by which, after entry into said piston, said transfer system is withdrawn before the injection in order to restore the tightness of the reservoir containing the formulation to be injected.

This withdrawal will be, for example, according to the device detailed hereafter, combined with deblocking the injection piston.

A certain number of other more precise applications, derived or resulting from the devices according to the invention, will be specified in the more detailed descriptions which follow.

The devices and processes which are subjects of the present invention can advantageously operate using a reconstitution process which directly allows an injection without prior degassing. Once reconstituted, the formulation can be used immediately at atmospheric pressure without risk of above- (or below-) atmospheric pressure; no risk, therefore, of atomization or accidental squirting of the product at the moment it connects with the injection needle. This, combined with the absence of degassing, eliminates significant concerns such as contamination on contact with the environment and the risk of accidental pricks, the needle no longer having to be handled in the open air before insertion. This needle can even be advantageously connected to the reconstituted formulation only after it has been introduced into the body, which allows the vein test to be carried out by simple sighting of the other end of the needle after insertion.

One of the most standard reservoirs corresponding to the existing standardization needs is the cartridge or injection cartridge, ending at one end in a standard piston and at the other in a sealed neck, a protective cap or septum or a stopper and sealed by a metal cap.

Similarly, the devices according to the invention can advantageously use such standard cartridges for their two reservoirs as well as the existing pistons and stoppers. The conditions for filling and sterility treatment for their two reservoirs can be exactly the same as those generally applied to this type of container.

Thus the device according to the invention provides a novel and simple solution which among other things answers the questions, problems and requirements raised previously.

Moreover, the use of the vacuum-based automatic rehydration system constitutes per se a direct check on the integrity of the primary pack containing the active ingredient, namely the reservoir or cartridge. Its VAC operation offers a unique guarantee that the a sepsis of the reservoir has indeed been preserved during storage. This check can be combined with a secondary packaging under vacuum which will provide the same check on the whole of the device and will optionally allow the vacuum check to continue for the duration of storage.

The descriptions which follow (general or more specific when based on the figures) represent only a few advantageous examples of embodiments of the device according to the invention, which can be implemented according to other specific versions also covered by the invention. In addition to a detailed possible device, certain other alternatives will therefore be presented.

This device, according to the invention, can be applied, subject to a few minor modifications but still according to the same mechanical principles, to numerous variations in the field of injectable material and in other therapeutic fields. Certain specific details concerning these other possible applications such as, for example, their use in a pen-injector, will be given according to their relationship with the inventive matter.

In the example described and according to an advantageous embodiment of the invention, the device is presented with a total separation of the two reservoirs, namely that receiving the non-liquid elements (here lyophilizate) and that receiving the liquid elements (here suspended aqueous medium). In other words, there is no physical link between the two reservoirs before use.

Said reservoirs can moreover advantageously be packaged separately and individually. However, as will be specified, it is possible to envisage the device in a pre-arrangement in which the two sub-systems are combined or even included in the same pack.

The process aspect of the invention concerns the details of the preparation and the packaging associated with the use of standard reservoirs and the use of the device, in particular around the lyophilizer.

Although the device of the invention could be realised with other types of reservoir and in particular with glass tubes, in the advantageous embodiment of the device described in detail, two standard cartridges, for example with capacities of 2.25 and 3.15 ml, will be used as reservoirs.

The cartridge containing the non-liquid part, here the lyophilizate, constitutes the proximal reservoir situated inside said device and directly in contact with the outlet zone of the injection needle. It is in this proximal reservoir, which in general contains the active ingredient of the preparation, that the reconstitution takes place of the formulation to be injected, which is then, in terms of arrangement, in a mode equivalent to the traditional use of injection cartridges, exactly opposite the double-tipped needle.

The cartridge containing the liquid part or aqueous injection medium constitutes the distal reservoir of the device. It is situated at the other end of the injection device and also serves as the piston rod during the injection of the preparation through the syringe which it forms with the assembly. It therefore penetrates to a greater or lesser depth into the interior of the body of the syringe device and into the interior of the proximal cartridge.

Located between these two cartridges are the various pieces or elements of the connection mechanism which can be fixed on the piston of the proximal cartridge. The whole is preferably arranged inside a plastic body which guides or controls certain of the functions and which protects the glass reservoirs.

The lower part of this exterior element which constitutes the body of the injection syringe which forms the device will preferentially have a cylindrical shape, and its upper part will comprise the finger-rest of said syringe. Each part can be a separate sub-element joined to the other at the moment of assembly. The lower part of this cylindrical body can also exercise a support and guiding function for the cartridge and the injection piston during the lyophilization and vacuum-packaging operations.

The proximal end of said lower part will support the injection needle which can be pre-fixed as represented below or, more conventionally, mounted on a base which will be attached to said proximal end. Advantageously, this end can therefore constitute a third external element fixed to the lower part.

The device is therefore presented below with a specific solution of a prefixed needle and screw-cap which avoids the risk of actuation before reconstitution of the formulation. It is obviously possible to use this device with any other needle and in particular non-pre-fixed needles, for example those of the standard type used on injectors or cartridge pens.

Similarly, for other applications (perfusion, ophthalmiatrics etc.), the device could be combined with a connector or transfer needle, a drip-feed or a spray.

On the distal side, the detailed solution keeps the liquid cartridge as a piston rod. In the case, for example, of a pen-injector, the whole of the body of the device can constitute the proximal part of the injector and it is possible to envisage withdrawing the distal cartridge after reconstitution and replacing it with the dosage mechanism of said pen, which would reseal the body of the device.

This solution is particularly advantageous given the precision of the total reconstituted dose and the small capacity of the pen-injector, without distal cartridge or bi-compartmental cartridge, which makes possible the use of the device according to the VAC procedure, thus allowing the case of a lyophilizate to be reduced to the simple and standard case of a solution.

For reasons of clarity and logical sequencing of the operations in a chronological order, after the general FIG. 1 of the detailed device according to the invention with the figures which follow, we will describe, in the first instance, the filling and packaging procedures (certain aspects of which constitute the second part, i.e. the preparation process of the invention), before specifying the device of the invention which originated from it. These procedures correspond to the assembly of the device of the invention which originated from it and allow said device and the functions of the elements which constitute it to be specified. We will finish, finally, in the figures, by describing the use of said device.

The precise and specific device represented by the following figures constitutes only one possible solution embodying the device and the process according to the invention, which is in no case intended to limit the general scope of said invention.

For example, the said lock elements represented hereafter could be replaced by a key or side-pin system capable of blocking the piston of the vacuum-packed cartridge not only on its glass base but also on the plastic sleeve which surrounds it. Said key could be unlocked (or unpinned) after reconstitution according to the VAC procedure. For reasons of convenience and space in the lyophilizer, said key system could be provided with a removable or independent handle or actuation grip.

Similarly, although one of the advantages of the devices according to the invention in terms of filling, sterilization and packaging, may be the physical separation of the two reservoirs, it is perfectly possible to assemble them in advance, either after sterilization (in aseptic conditions), or before sterilization (with a post-sterilization of the whole). In the case of the assembled solution, the liquid cartridge can be provided with a blocking/deblocking device in the body of the syringe which prevents its being accidentally handled. It can also ensure (for example by a seal) the aseptic sealing of the body of the syringe.

In the solution represented by the figures, it is also possible to provide a device or element which protects the membrane or the septum of the cartridge either of the flip-off type, or a system, for example retractable on the tube, which will protect this septum until the introduction of the neck into the syringe body. Similarly, alongside this body and for example at the finger-rest, it is possible to provide a means of protection, removable or piercable for example, which ensures that the transfer needle remains aseptic.

Finally, the device is presented in a pre-fixed needle solution. It is possible to design the device according to the invention as simply equipped with a stopper on the proximal side of the head of the cartridge; a stopper which will be withdrawn after reconstitution of the mixture, and replaced by a needle the fitting of which by its base can ensure the piercing of the membrane or stopper of the cartridge. This piercing can be carried out either by a double-tipped needle or by a plastic tip, an element of the base whose channel will be connected to the needle. In order to specify the general part of the invention in terms of the device and preparation and packaging process, following the detailed example, other possibilities will be presented and their treatment process summarized.

One solution, adaptable to treatment in aseptic conditions and to smaller volumes, will thus be mentioned. A simplified solution which is adaptable to small volumes and pen-injectors will also be described. Finally, an alternative solution to the detailed solution, in which certain automated aspects of the mechanism are dispensed with in favour of a general simplification. The specific process of the invention will be stated each time.

FIGS. 1 to 13

Figure 8:
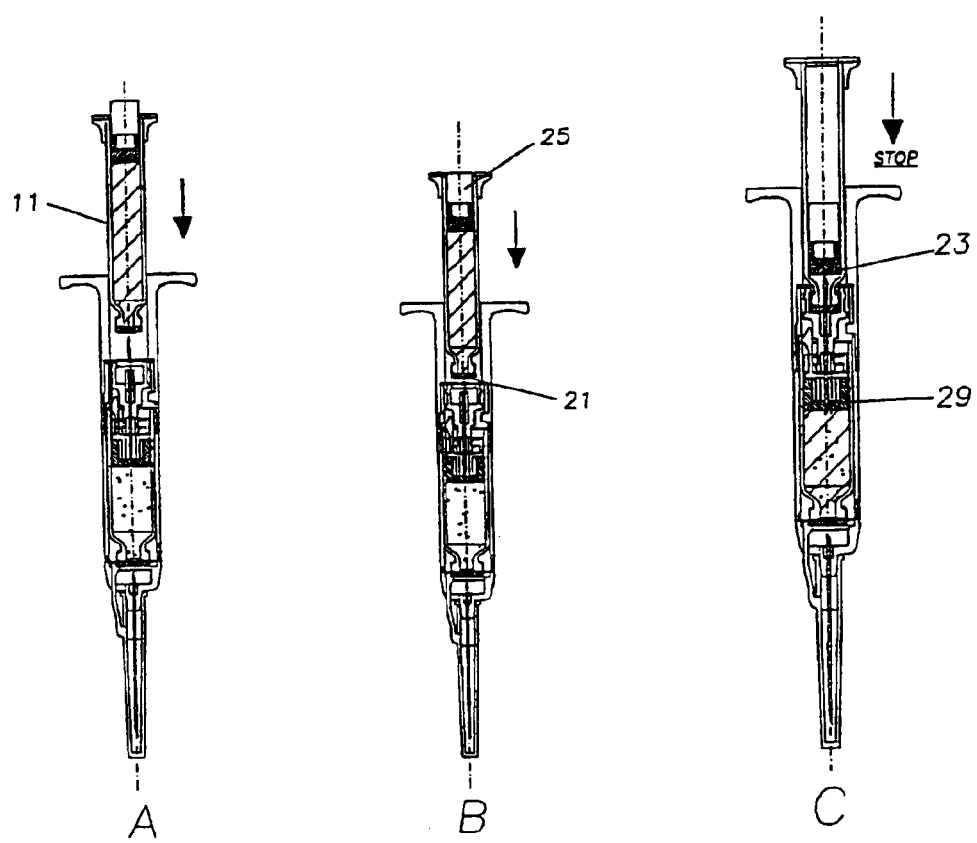
Figure 9:
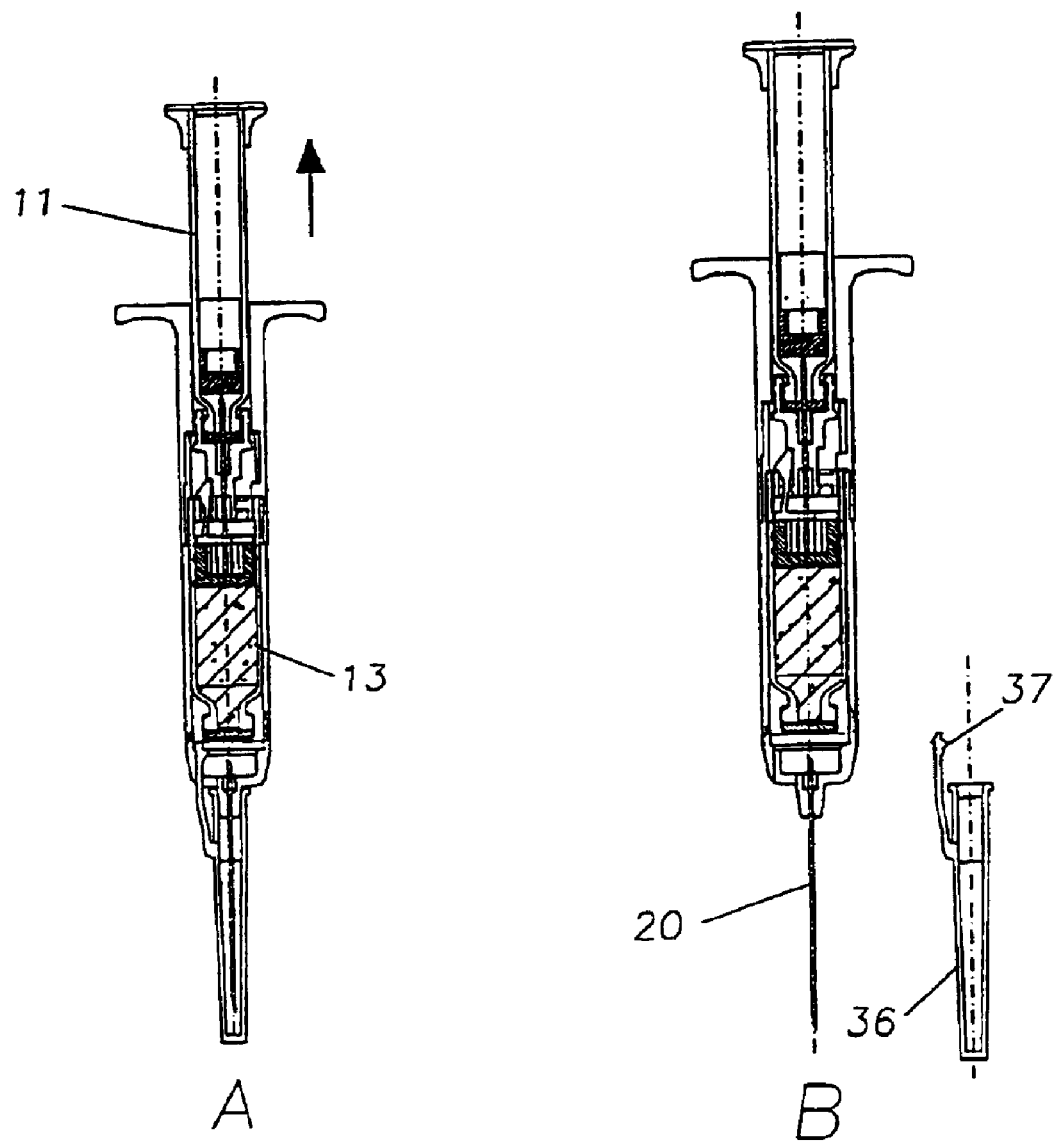

FIGS. 8 and 9 describe, after the joining of the two sub-systems of the device (namely the body of the syringe containing the cartridge of solid material and the rod of the syringe which is the cartridge for the liquid), the automatic VAC reconstitution and the operating mechanism of the device of the invention.

Figure 10:
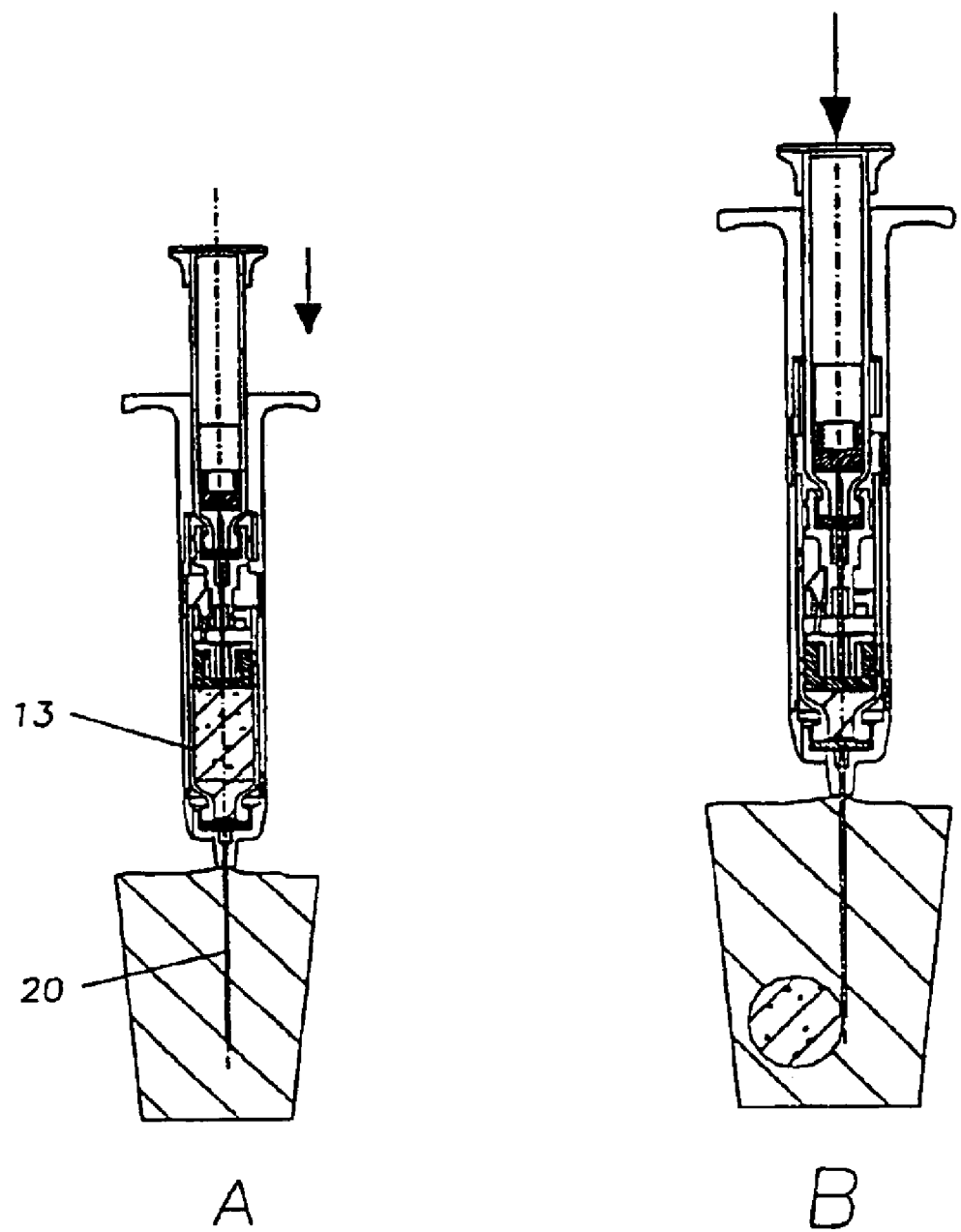

FIG. 10 represents the injection into the body of the fonnulation reconstituted in the device of the invention.

Figure 11:
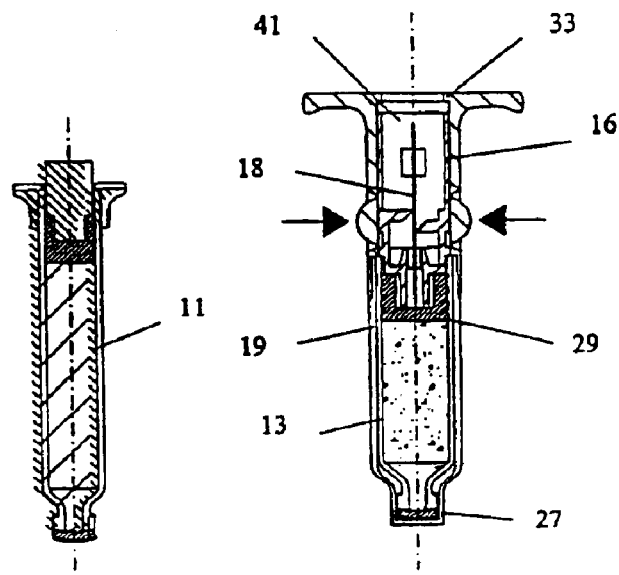

FIG. 11 represents an alternative device around another transfer mechanism which can be used in aseptic conditions.

Figure 12:
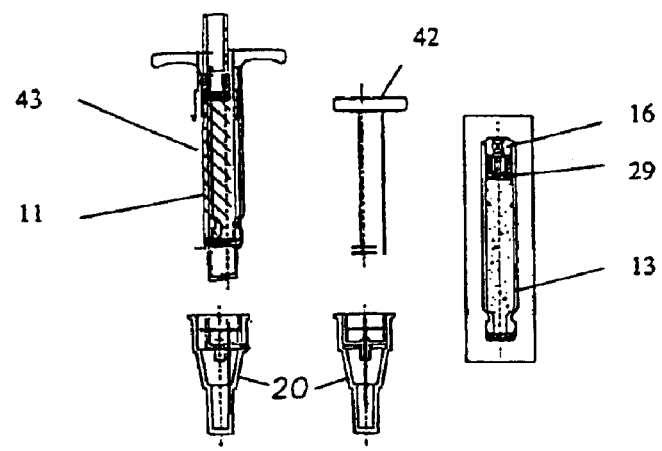

FIG. 12 illustrates a simplified device for small volumes and for pen-injectors.

Figure 13:
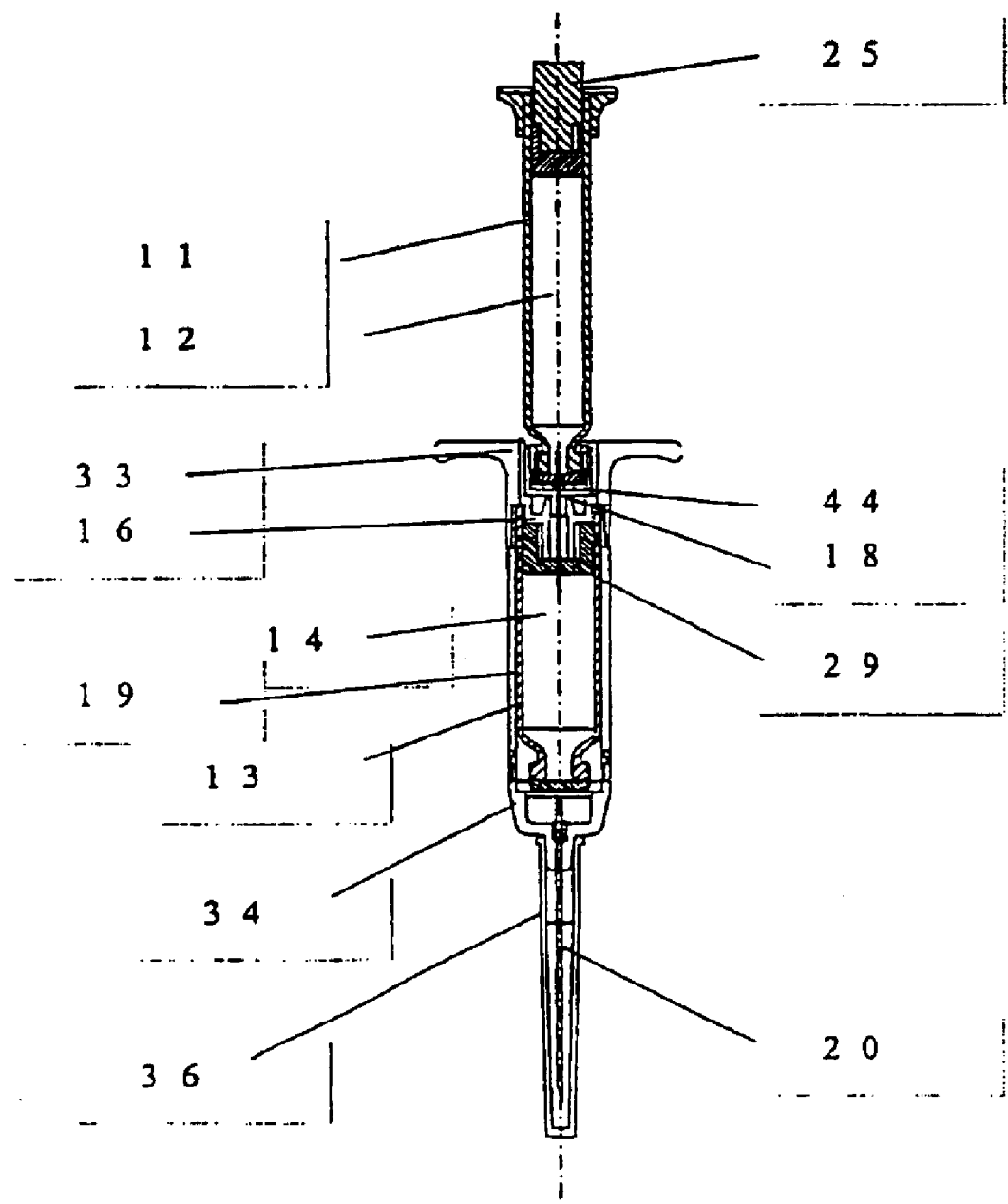

Finally, FIG. 13 represents the application of the simplified device to the case of the formulation and the volume of the previously detailed device.

DETAILED DESCRIPTION OF THE FIGURES

Figure 1:
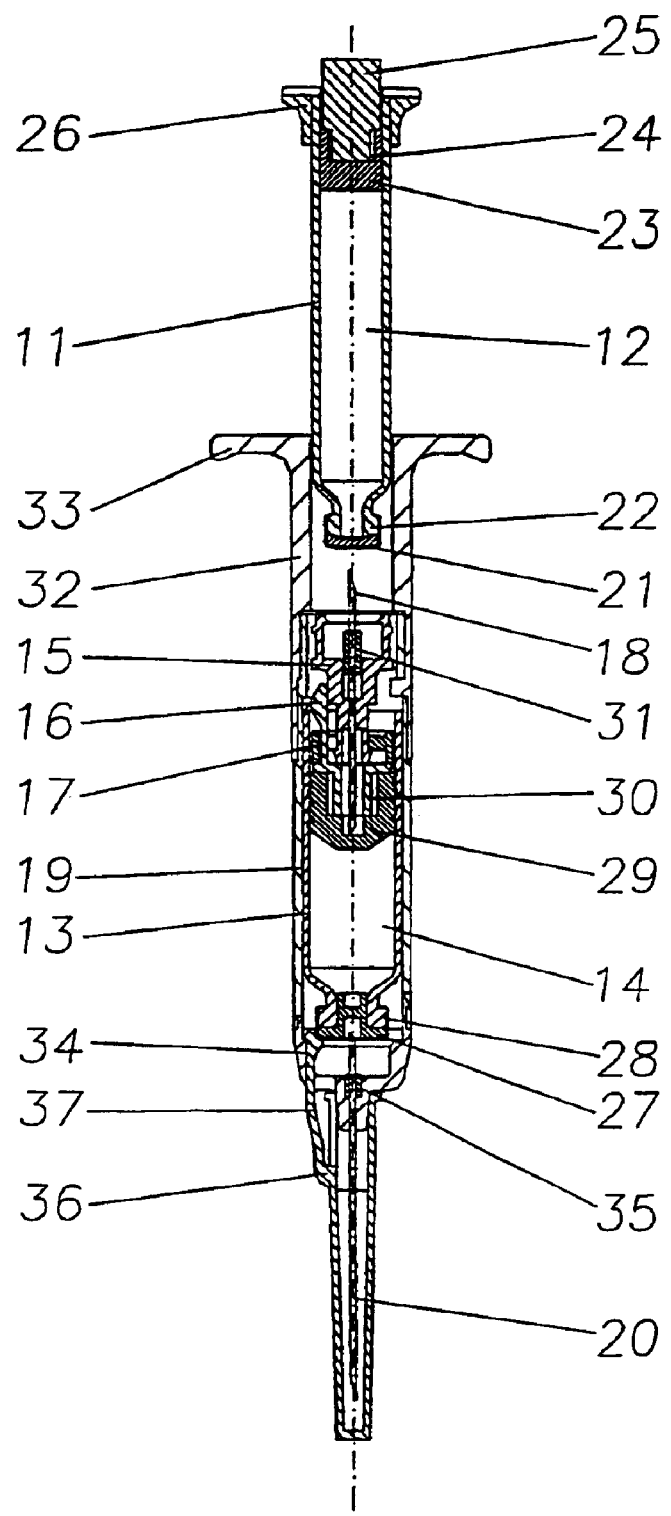
FIG. 1 represents a general view of the device of the invention after installation of the piston rod formed by the liquid cartridge and before actuation.

FIG. 1 represents a specific form of the device allowing the realization of a medicinal solution or suspension, a solution of peptides or proteins for example, or an injectable suspension of PLGA microspheres allowing the sustained release of an active ingredient (delayed forms), according to the VAC process, from 2 basic reservoir elements, in this case cartridges. In particular, FIG. 1 represents this device before reconstitution; once installed, the distal cartridge acts as a piston rod and gives said device a very similar appearance to a standard syringe. This version corresponds to the solution for 2 ml maximum volume to be injected; the distal reservoir can be filled to a greater or lesser degree and determine the reconstituted volume.

This syringe device has a first container 11 constituted by the cartridge in which a solvent or aqueous medium 12 is stored, a second container 13 constituted by the cartridge in which the solid or lyophilizate form 14 is vacuum-packed, 4 transfer elements, namely the upper key 15, the lock 16, the lower key 17 and the transfer needle 18, and finally a sleeve 19 in which the reservoir 13 is located and which marks the point of entry at the distal end of the reservoir 11, serving as piston rod, and on which the injection needle 20 is fixed at the proximal end. It will be noted that the lyophilizate 14 which corresponds in the example to a suspension of microspheres (delayed form) can be replaced by any lyophilizate of injectable solutions, by a powder or any other vacuum-packed solid forms such that they can form, after reconstitution, a liquid, a gel or a paste-like form which can be used in said device.

The first container 11 serving as reservoir or distal cartridge and piston rod of the syringe, is preferably stored and packed away from the rest of the syringe, for example in an individual pack. All the rest of the device can advantageously be packed together in a second pack.

The cartridge 11 of the first container which contains the liquid medium 12 is sealed at its two ends in a standard manner. At its proximal end, the sealing means will be for example a membrane or a sealing disk 21 attached to the neck of the cartridge by a sealing cap 22 pierced in its centre and which can, for example, be made from metal. This solution, equivalent to that used in dental cartridges among others, will in particular allow filling by overflowing, preventing any bubbles of air inside the liquid. At its distal end, the cartridge 11 is sealed by a piston 23 which can be a standard injection piston, made for example from rubber or polybromobutyl. This piston has an internal screw-thread 24 where the piston rod is usually attached.

In the case of the device, this screw-thread 24 serves to attach, by screwing, the short drainage rod 25 which will activate the rehydration by " unsticking"the piston 23 and will drain the transfer needle 18, by filling it, after piercing the membrane 21. The length of said rod will depend on the volume of the liquid in the cartridge 11. It will exceed said cartridge by a length which allows the piston 23 to be displaced by a distance at least sufficient for the displacement of the quantity of liquid necessary for the drainage.

Moreover, this first container 11 also carries, attached to the distal glass end of the cartridge, a finger-rest 26. This finger-rest is the zone where the thumb comes to rest during the actuation or extemporaneous reconstitution operations. It can have the following different functions: it terminates the cartridge 11 like any syringe; in its function as piston rod of the device, it prevents cavities from being created by the displacement of the piston 23 while pressure is being exerted by the thumb, with the help for example of small openings or escape passages situated under the support zone and communicating with the inside of the cartridge 11, behind the piston 23. It provides a grip during the unlocking of the second container 13, after reconstitution due to a rearward movement of the assembly 11. Finally, the finger-rest 26 can serve to lock or block the piston 23 and its drainage rod 25 rearwards to prevent them from being extracted from the cartridge 11 or the drainage rod 25 from being unscrewed.

The second element of the device forming the body of the syringe surrounds the cartridge 13 containing the solid or lyophilized part 14 of the vacuum-packed formulation. This cartridge 13 can also be sealed at its two ends in a standard manner. The proximal end, facing the injection needle, can be blocked by a membrane or plug. According to an advantageous embodiment which allows a standard lyophilization treatment, it will be sealed by a stopper 27 engaged in the neck of the cartridge. This stopper 27 can ensure a better tightness of the seal and the maintenance of the vacuum in the cartridge 13; it will optionally allow the reduction of the dead volumes of the injection cartridge; finally, it can be used like standard stoppers of bottles of lyophilized forms, i.e. be pre-positioned after filling of the medium then freeing apertures or escape passages in order to eliminate the liquids, by sublimation during the lyophilization and can then stop the cartridge under vacuum in the lyophilizer using a customary mechanism. However, this standard possibility is not that described in the packaging process according to the invention.

This packaging process according to the invention constitutes a new advantageous embodiment in that it allows the pre-sealing of the cartridge at its neck, for example with a standard membrane or plug, sealed by a metal ring, then the filling and lyophilizing of same from the rear before stopping it by its usual injection piston. Thus, the sealing elements are completely standard; operation is easy, from the largest opening, and any dead volume is avoided.

The membrane or stopper 27 is sealed onto the neck by a cap 28 which can be made of metal. The internal bevel of the injection needle 20 will connect the formulation to the needle, through this membrane or this stopper, at the moment of the injection.

At its other end, the container 13 is stopped by a piston 29 which can be a standard cartridge piston made from rubber or polybromobutyl. This piston 29 has an internal screw-thread 30 or any other type of attachment capable of attaching it firmly to a part of the lock 16 forming the locking-unlocking mechanism with the keys 15 and 17. Here, for example, the base of the lock 16 is screwed onto the screw-thread of the piston 29. This lock 16 as well as the upper and lower keys are hollow, so as to contain, allow to circulate and monitor the movement of the transfer needle 18 during the actuation by transfer of the liquid. It is the cartridge 11 acting as piston which will activate the whole of this transfer mechanism with the part of its neck which will be connected thereto. The lock 16 has, at its other end, support arms which come to rest on the glass base of the distal end of the cartridge 13 in locking position. These bases prevent the pressure generated by the vacuum in the cartridge from carrying the piston downwards.

The lower key 17 surrounds the support arms of the lock. This key is free in locked position. During the actuation, by introduction of the upper key 15, this lower key is firmly attached to the proximal part of the upper key. At this moment, the support arms of the lock 16 block the introduction movement, permitting only a rearward movement withdrawing the assembly comprised of cartridge 11 plus transfer elements.

During this withdrawal movement, the lower key 17 releases the lock 16 by gripping the arms of the lock and blocking the transfer mechanism which then allows the injection.

The transfer needle 18 inside the transfer mechanism, and more specifically the upper key 15, comprises a base 31 the role of which is to clip the needle 18 into the key 15 only after said needle is filled with the liquid 12 and before the piston 29 is pierced.

For a totally reliable operation of the actuation, the length, the diameter and the type of bevel, on the cartridge side and piston side, can be optimized in such a way that the transfer needle systematically penetrates, firstly through the membrane 21 of the cartridge 11 and, only then, through the piston 29. For example, the needle can be finer on the cartridge side 11 with a long, more penetrating, bevel.

Similarly and according to the same objectives, and to guarantee more tightness during the penetration into the chamber under vacuum, the membrane 21 can be finer than the base of the piston 29. The latter presents a thickness sufficient to guarantee the tightness during the penetration of the needle 18 and, in particular, a thickness greater than the length of the bevel of this needle, on the piston side 29.

The rearward unlocking mechanism also allows, after VAC rehydration, the withdrawal of the needle 18 from the piston 29. During the injection, the needle 18 remains blocked in the upper key 15 and the blocking of the mechanism by the withdrawal or clamping of the locking arms 16 prevents said needle 18 from re-crossing the piston 29.

This assembly comprising cartridge plus transfer elements is contained in the case or sleeve 19 which forms the body of the syringe. According to a preferred mode of arrangement of said sleeve, it is constituted by three sub-systems locked or clipped into each other at the moment of assembly.

The principal or central part of the sleeve 19 contains the cartridge 13 Attached to its distal end is the end of the sleeve 32 which can comprise the finger-rest part of the syringe or grip 33. Moreover, this end can have the rearward locking and blocking mechanism of the cartridge 13 and of the transfer mechanism, thus preventing any withdrawal after assembly.

The end or stopper of the sleeve 34 is attached to the proximal end of the central part 19. It is to this end that, in the version of FIG. 1, the injection needle 20 is attached at its base 35. The stopper or cap protecting the needle 36 can also be attached at the end 34.

This solution allows a device to be realized which is completely equipped, in particular one with a pre-fixed injection needle without having a problem with the length and the position of said needle during the packaging of the formulation.

In the version shown, this cap is blocked by a lock 37 held by the head of the cartridge 13. In this way, the cap 36 cannot be withdrawn nor the cartridge 13 connected to the injection needle 20 before the transfer mechanism has been completely realized i.e. until withdrawal, after VAC hydration.

The other specific functions of certain elements of the whole are explained in the description of the figures which correspond to them.

An essential variant of FIG. 1, in the case of use for a multi-dose system of the pen-injector type, could be the attachment of interchangeable needles at the stopper end of the sleeve 34 which would then seal the end of the pen-injector.

In this version, during the withdrawal after reactuation, the cartridge 11 could be removed and replaced by a standard dosage and injection mechanism which would be attached, by its container, to the sleeve 19 or to its end 32, for example, by screwing. This container of the dosage and injection mechanism would thus seal the pen-injector in its distal part.

In the same way as the vacuum in the cartridges provides an integrity check, the whole of the part of the body of the syringe of the device can be vacuum-packed and thus the same check performed, with a thermal isolation and a better stability or inertia as an advantage. This pack vacuum can, for example, be greater than the vacuum in the cartridge 13 to ensure the continuity, or double security, over the period of storage.

Figure 2:
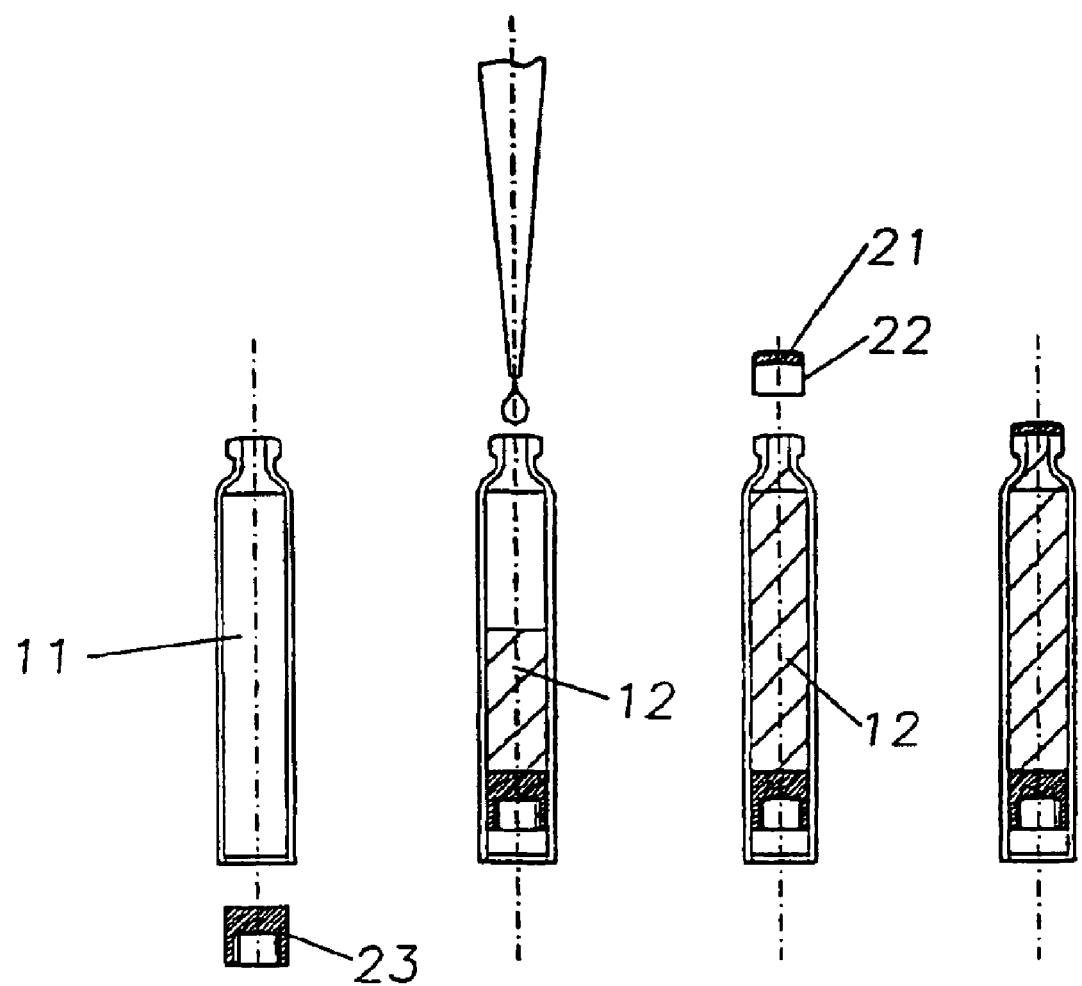
FIGS. 2 and 3 represent schematically the standard filling process around the standard cartridge containing the liquid phase, then its specific assembly so as to be capable of then being used in the device of the invention.

FIG. 2 represents schematically a standard filling procedure for the cartridge 11 containing the liquid part of the formulation. The piston 23 is installed beforehand and its position in the tube of the cartridge 11 precisely determines the liquid reconstitution volume. This liquid volume 12 is added, according to a standard process which can be realized on automatic machines. The cartridge 11, once filled right up to the neck, is then sealed by a cartridge 22 containing for example a membrane 21, according to a method which is equally standard and automatable. This process, which can be realized by overflow, prevents the presence of gas inside the sealed cartridge.

Figure 3:
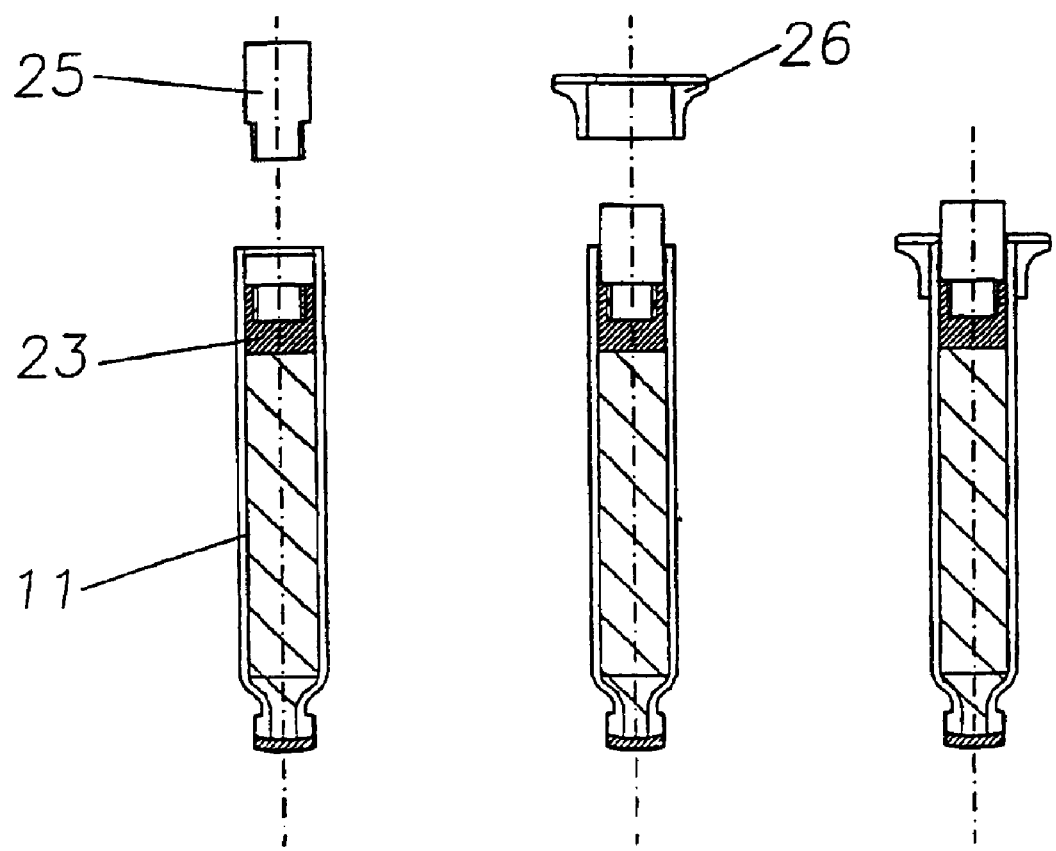

FIG. 3 represents the insertion of the drainage rod 25 into the cartridge 11 for example by screwing onto the piston 23. The finger-rest 26 is then attached or clipped onto the glass base of the cartridge tube. It can thus prevent any removal of the piston 23 and of the rod 25 and prevent the disassembly of said rod 25. The thus-assembled whole can be sterilized in a standard manner, for example, by autoclaving.

Figure 4:
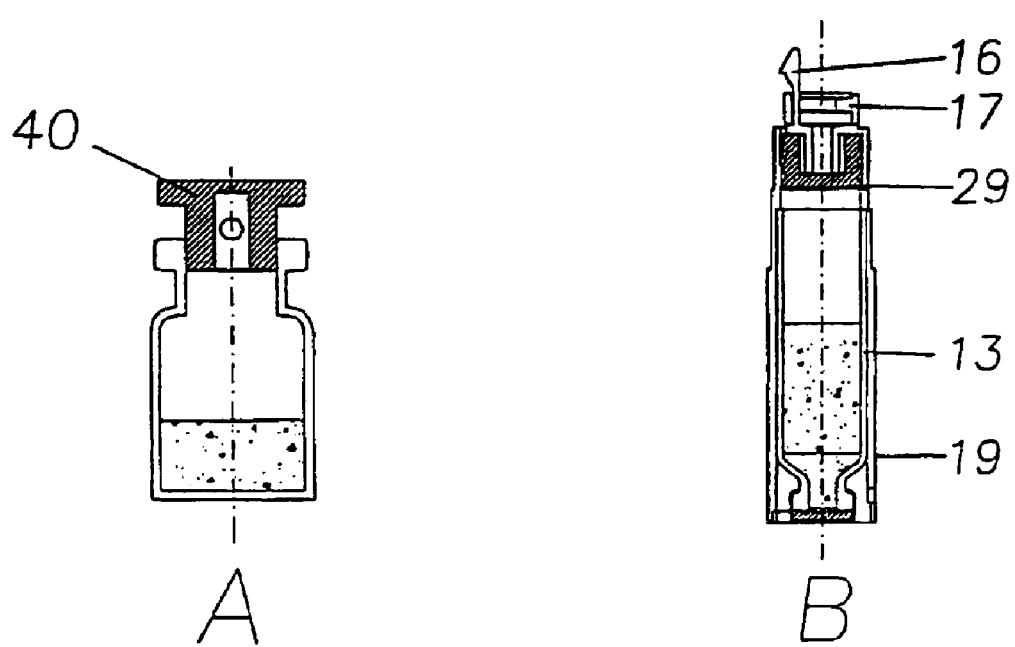
FIGS. 4 to 6 illustrate the packaging stages of the solid phase of the formulation in a standard cartridge and in the particular case of a dispersion in a lyophilizate.

FIG. 4 represents schematically a comparison between a standard lyophilization bottle and the device according to the invention, which constitutes a part of the invention corresponding to the procedure of lyophilization and packaging at the rear or through the distal part opposite the proximal side of the injection and the neck of the cartridge. In a standard bottle A, the stopper 40 is pierced by holes and apertures which allow its positioning on the neck before lyophilization and its sealing by pressure of the racks in the lyophilizer. The aim of the device according to the invention is to allow such a lyophilization, no longer with a standard bottle of type A but with a standard cartridge 13 as shown in B. To do this, as we explained previously, it is possible to use a stopper on the neck of the cartridge 13 equivalent, on a smaller scale, to the stopper 40 of the bottle A. In this case, the transfer mechanism where at least one locking element attached to the piston 29 is pre-positioned at the distal end of the tube of the cartridge 13 and the lyophilization is carried out by opening the neck. This solution removes the lyophilizate from the heat-exchange tray and isolates it partially by the piston 29 thus rendering the process more difficult. Moreover, it complicates the filling by the narrow neck and does not allow a 100% filling.

In the solution of the process of the invention shown here, in particular to optimize and facilitate the filling of the cartridge 13 and to facilitate all operations for the preparation of the lyophilizate, the procedure is different. The cartridge is sealed beforehand with its stopper 27 by a cap 28 (cf. FIG. 1); it is filled with the preparation to be lyophilized through its large distal opening, up to the base of the neck. It is thus possible to use all standard cartridges in order to pack a lyophilized form there, even the smallest ones, and also to operate all the possible arrangements of the future lyophilizate, such as for example, the filling of two successive layers either because they are incompatible or because the second serves to prevent the dead injection volumes. The injection piston 29 stops the cap at the end of lyophilization; unlike stopper 40, it is not equipped with escape passages or openings synonymous with dead volume and it is not pre-positioned on the glass base of the cartridge 13 but on a cartridge support 19 in this reversed position which serves to guide it. This cartridge support can advantageously be the central part of the sleeve 19 or body of the syringe. The advantage is to have here a perfectly cylindrical shape which will maximize the saving of space in the lyophilizer and the total filling of the useful volume of the cartridge 13. The sleeve 19 in its distal part has clip zones with the part 32 of the body of the syringe which serve, here, both to hold the piston 29 and the opening in the cartridge during lyophilization. The piston 29 is pre-fitted in this distal part of the sleeve 19 at least with a part of the transfer mechanism, namely, here, the lock 16 and the lower key 17. This guiding of the sleeve 19, once the device is assembled, serves here to block or stop the movement of the cartridge 13 in the body of the syringe.

This reverse lyophilization therefore offers a whole range of advantages whilst allowing a standard process with a good contact with the cold source.

Figure 5:
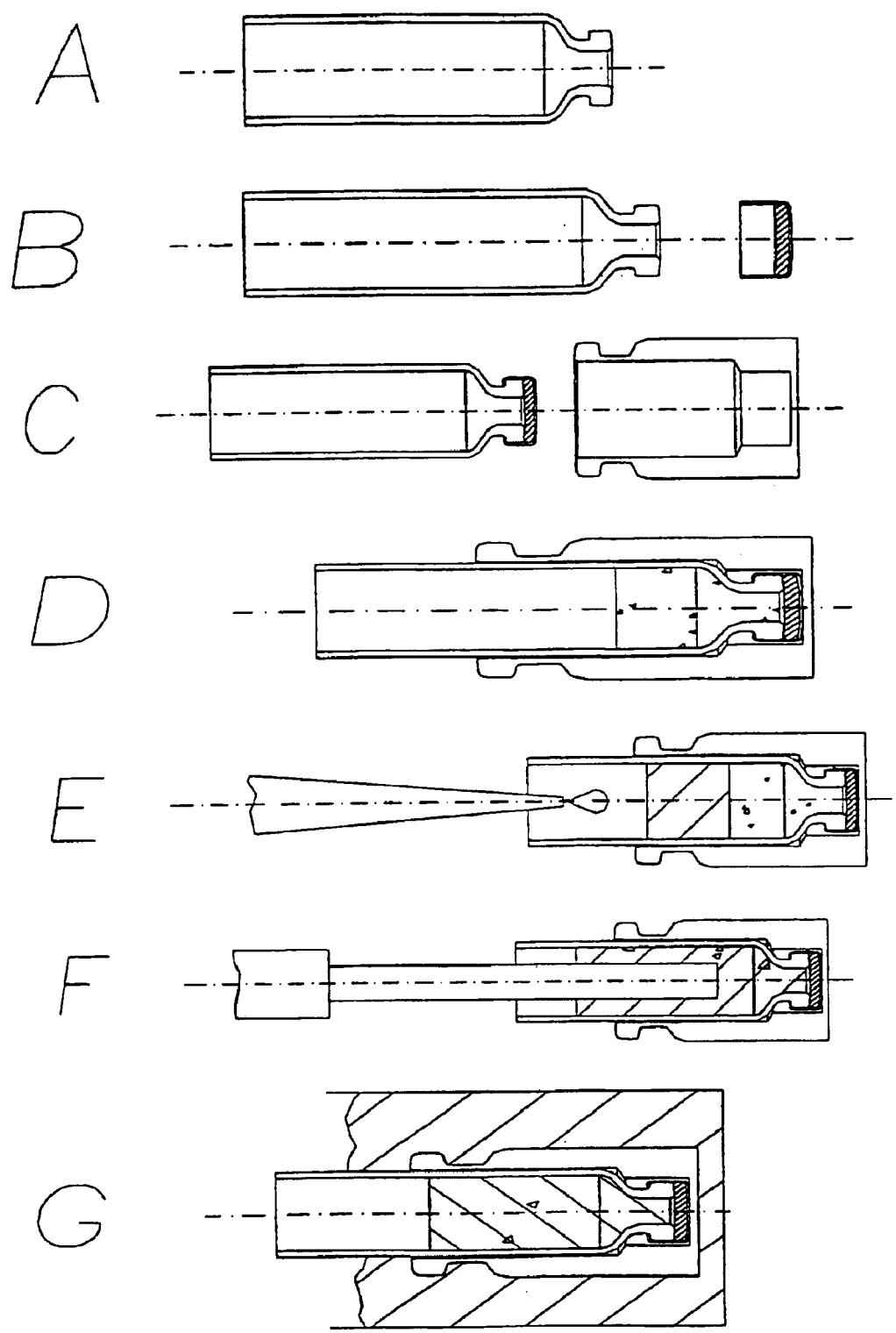

FIG. 5 illustrates the realisation of a specific packaging operation of a formulation to be lyophilized carried out in a cartridge according to a process equivalent to that traditionally used with a bottle. In A, the cartridge 13 is washed and siliconized, in B, it is sealed by its cap and membrane, in C, it can be fitted into a receptacle accommodating the shape of the bottle 40, in D and E, the constituents of the mixture are easily introduced through the base, in F and G, all equivalent treatments can be carried out with the bottle with the same guarantee of height to the outside. A treatment with ultrasound is represented schematically here. In the same manner, the mixture (vortex) or the suspension could be stirred vigorously before freezing.

Figure 6:
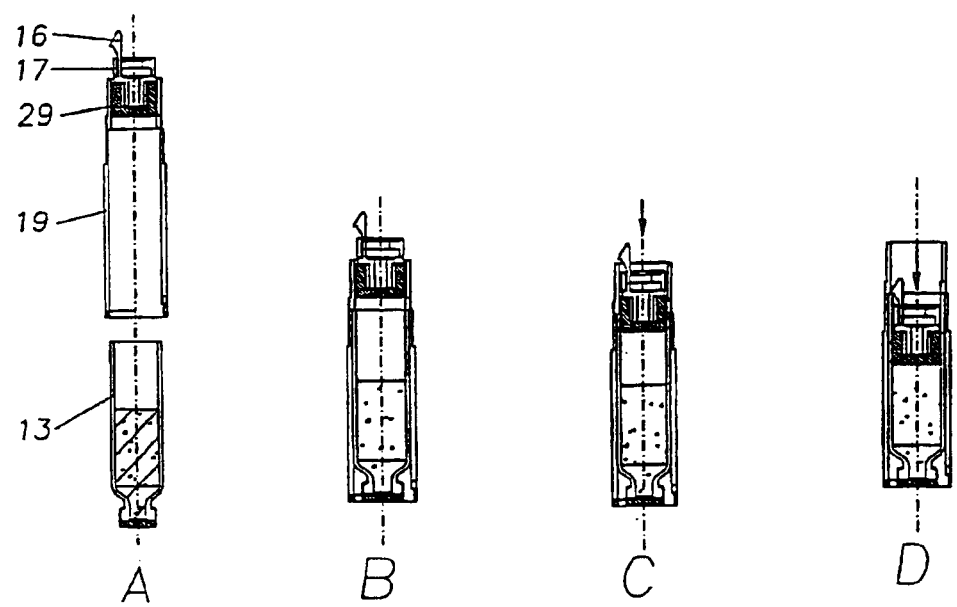

FIG. 6 shows a cartridge 13 filled with the mixture to be lyophilized, frozen beforehand or not. In A, this cartridge 13 is introduced into the sleeve 19 which serves as a support for it. In B, all the stages of the lyophilization cycle are usually carried out in the lyophilizer. In C, at the end of lyophilization, and still under vacuum, the piston 29 is introduced inside the cartridge tube 13 by standard pressure in the lyophilizer on the lock 16. At this point, the lyophilizate is completely isolated from the outside by the sides of the piston 29 in tight contact with the wall of the cartridge tube. In D, the vacuum inside the lyophilizer is broken, thus ensuring a return to atmospheric pressure. Under the action of this pressure, the piston 29 and the lock 16 will continue to fall in the tube of the cap 19 thereby providing a visual and individual check on the existence and quality of the vacuum in the cartridge. This movement of the piston will be stopped by the support of the arm of the lock 16 on the cartridge 13. The sealed element, thus constituted, then becomes an integral part of the device according to the invention.

Figure 7:
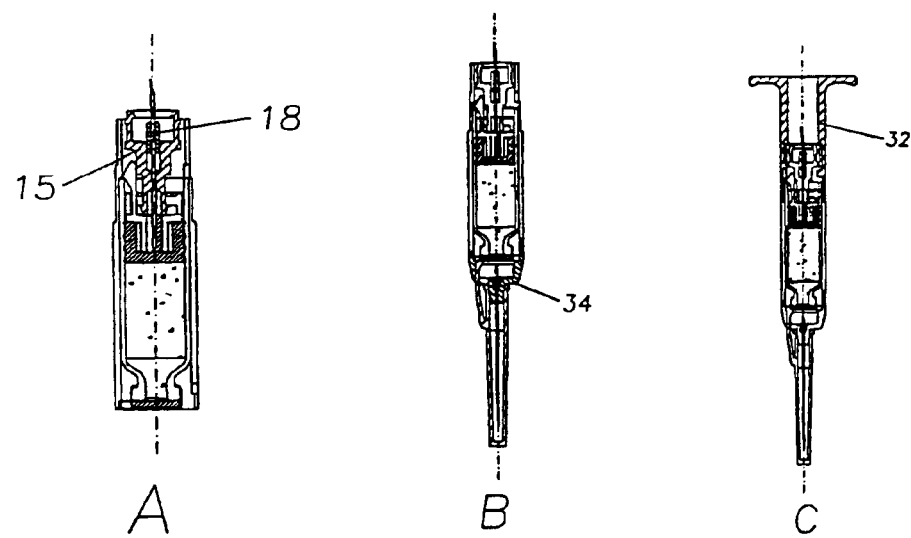
FIG. 7 represents the assembly stages of the proximal part of the device around the solid or lyophilized form.

FIG. 7 shows the sequence of the assembly operations for said device. In A, on the base of element D of FIG. 6, the other parts of the transfer mechanism are assembled, namely the upper key 15 in which the transfer needle 18 is pre-fitted. This upper key can have a clip ring for the head of the cartridge 11, higher around the needle to protect it during handling. In B, the proximal part or stopper of the sleeve 34 which includes beforehand the injection needle 20 and the cap 36 are attached, for example by clipping. In C, finally, the third part of the body of the syringe, namely the distal part of the sleeve 32, is attached. This part of the body of the syringe, can then be packed individually and post-sterilized, for example by gamma-irradiation.

FIG. 8 shows the reconstitution stages of the formulation contained in the device of the invention. In A, the cartridge 11 is introduced into the body of the syringe. In B, the reconstitution is activated by pressure on the drainage rod 25. The first operation is therefore the piercing of the disk 21 then the filling of the needle. In C, using the same application of pressure to the rod, finally, the piercing of the piston 29 is carried out. At this point, the movement is then blocked and the preparation is reconstituted automatically with the descent of the piston 23 in the tube of the cartridge 11.

FIG. 9 firstly shows, starting from stage C of FIG. 8, in A, the unblocking by removal of the piston rod constituted by the cartridge 11. This operation has already been described in the functioning of the transfer mechanism. It pulls the cartridge 13 slightly to the rear as far as its stop on the sleeve. In B, the removal of the cap, made possible by the release of the cap 36 at its blockage 37, is carried out by slightly withdrawing the head of the injection cartridge 13. Only now can the injection cartridge 13 be connected to the injection needle 20.

FIG. 10 represents schematically the injection according to a completely standard method. Given that the device according to the invention allows a preparation which does not require drainage prior to injection, it is possible, before A, to inject the needle 20 prior to its connection to the cartridge 13. This stage can also serve as a direct vein test, for example, in the case of IV or IM injection by sighting any return of blood from the internal bevel of the needle before connection to the formulation. In B, at the end of the injection, the mechanism can be blocked to avoid any subsequent handling.

FIG. 11 represents another possible realization of the device according to the invention adaptable to treatments under aseptic conditions (in particular for filling) and smaller volumes. The use of this device does not require any aseptic assembly after sealing into the lyophilizer, the device and its constitutive elements then being isolated from the outside.

During the lyophilization process according to the invention the lyophilizate cartridge 13 is installed inside the sleeve 19 which is then positioned in proximal position around the neck of the cartridge which it supports and which bears, at its distal end, the lock 16 sealed at one end by the piston 29 and at the other end by a film 15 with the transfer needle 18 inside.

At the end of lyophilization, the reservoir is sealed by the piston 29 by bearing on the lock 16 and with the help of the guide zones of the sleeve 19 (not shown). The device is then completely locked by the head of the sleeve 27 and the finger-rest 33.

The treatment of the liquid cartridge 11 is similar to the example detailed previously. At the moment of use, the cartridge 11 is introduced through the film 41. It connects and drains the needle 18 before piercing the piston 29 for the VAC rehydration.

Once this operation has been carried out, the lock 16 is unscrewed by bearing on the area of the sleeve 19 marked by the arrows, thus leading to the rupture of the thin walls and the clipping of 2 arms which will retain the lock and curve the needle 18 then allowing its extraction from the piston 29. The injection needle can then be installed on the head 27 and the injection carried out by the cartridge 11 serving as piston rod 29.

FIG. 12 illustrates another representation of the device according to the invention for the packaging of a solid form from the rear and its rehydration process through the injection piston of the device.

Here, the lyophilization process from the rear, according to the invention, is carried out on the cartridges 13 which have been previously capped and installed in a lower support (not shown) indexed to the upper support (not shown) of the piston 29 and lock 16. At the end of lyophilization, the piston 29 and its lock 16 are introduced into the cartridge 13. Another preferable solution according to the process of the invention consists of replacing these upper and lower indexed supports by individual supports (21) for each cartridge. These individual supports can then fulfil the role of receptacle as described in FIG. 5. In addition, these supports can be directly used in the lyophilizer and can constitute the base of a pack realized with the upper individual support (22) of the piston 29 and of the lock 16.

After lyophilization, the individual lower (21) and upper (22) supports close to constitute, in the lyophilizer, the cartridge pack.

The liquid cartridge 11 is prepared as described previously; it can have a drainage rod but not necessarily a finger-rest. A sleeve 43 and a piston rod 42 can also form part of the device. Two injection needles 20 (represented here in their cap) of the disposable needle type for a pen-injector (for example Micro Fine® from Becton Dickinson) are also necessary for its use.

In the case of the use of this device as a single-dose syringe, the cartridge 11 is introduced into the sleeve 19 as represented in FIG. 12, a needle 20 is fixed and the rehydration is carried out by piercing the piston 29 through the lock 16.

The sleeve 19 is then separated from the cartridge 11 and the lock 16 is unscrewed using the base of the needle 20 then placed in the cap. The sleeve 19 can have lateral openings allowing the release of the cartridge 11 and its reuse for the injection of the preparation reconstituted in the cartridge 13 thanks to the addition of a piston rod 42 to the piston 29 and the second needle 20.

In the case of the use of this device as cartridge of a multi-dose pen-injector, the cartridge 11 is introduced into the proximal part of the pen which could here be symbolized by the sleeve 19, a needle 20 is fixed to it and the rehydration and withdrawal of the lock 16 on the cartridge 13 are carried out as previously. The cartridge 13 then replaces the cartridge 11 in the proximal part of the pen for a standard use of the latter as with the cartridges for products in solution.

FIG. 13 shows a simplified use of the device according to the invention in the case of a formulation equivalent (in volume and composition) to that of the detailed example. The device can therefore function with the same cartridges 11 for the liquid part of the formulation 12 and 13 for the lyophilized part 14 as those represented in FIG. 1.

The essential difference concerns the connector lock 16 which is screwed to the injection piston 29 and made in one piece. No assembly operation is necessary at this stage before sterilization. Similarly, it is possible to avoid packaging before gamma irradiation.

The cartridge 13 is installed before lyophilization in the sleeve 19 which will serve as a guide during sealing of the piston 29. The head of the syringe 34 constitutes the base of the needle 20. It can be fitted tight with the cap 36 on the sleeve 19 for example by means of an O-ring seal between the cartridge 13 and the sleeve 19.

In this case, no packaging is necessary and the device is closed between the cap 36 and the connector lock 16. The finger-rest 33 can be clipped onto the distal part of the sleeve 19.

The use of this device, according to the invention, consists of fixing a standard needle 18 of the disposable-needle type for a pen-injector (for example Micro Fine® from Becton Dickinson) onto the screw-thread of the sleeve containing the liquid cartridge 11 or, as represented here, onto the single screw-thread 44 firmly fixed to the cartridge 11. The assembly is then introduced into the connector lock 16 then through the piston 29 by bearing on the drainage rod 25. After VAC rehydration, the cartridge 11 is withdrawn by unscrewing with the transfer needle 18 and the lock 16; another solution consists of lengthening the arm retaining the lock on the cartridge so as to clip the arms of the connector lock 16 at that point, only after the needle has disappeared into said lock. The cartridge-connector lock assembly is then unscrewed from the piston 29. A piston rod, which can be the cap 36, is fixed to the piston to carry out the injection.

Principal Preferred Embodiments of the Invention

The invention therefore firstly relates to a device of syringe type actuated by a piston in order to reconstitute a preparation, in solution, in suspension or in dispersion in a liquid inside a reservoir sealed by a piston and forming part of the body of said syringe, characterized in that the non-liquid part of said preparation is packed beforehand inside said reservoir of said syringe and the liquid part of said preparation is separated beforehand from said reservoir and said syringe, in which the reconstitution of said preparation is carried out by the transfer of said liquid part through said piston of said reservoir.

According to preferred variants of the invention, said device can additionally have at least one of the following complementary characteristics:

1) said liquid and said non-liquid are packed inside standard injection reservoirs such as glass tubes or cartridges;
2) said device includes characteristic 1) and is moreover a single-dose or multi-dose syringe of the pen-injector type;
3) the transfer during said reconstitution is carried out through a tip, a duct, a tube or a hollow transfer needle introduced into said piston;
4) said piston has a blocking mechanism on said reservoir preventing it being driven in before and during said reconstitution of said preparation, which blocking mechanism can also optionally be the connector of said liquid part on said reservoir of said syringe;
5) said device has characteristic 4) described above and said blocking mechanism is screwed onto said piston;
6) said device has characteristic 4) or 5) and said blocking mechanism can be deactivated, preferably after the reconstitution of said preparation;
7) said device has characteristic 6) and the deactuation of said blocking mechanism also corresponds to the withdrawal of said transfer needle from said piston;
8) said liquid part is in a container which serves to actuate said transfer into said reservoir of said syringe through said blocking mechanism;
9) said device has characteristic 8), said container then also serving as injection rod to said piston;
10) said device has characteristic 9), said standard reservoirs being glass cartridges;
11) said liquid is packed in a reservoir the piston of which is actuated by a short rod allowing the displacement of said piston to be initiated and said transfer element to be drained before injection into said reservoir of said non-liquid;
12) said device has characteristic 11), said reservoir of said liquid being moreover equipped with an end preventing its blockage by the thumb of the hand;
13) said non-liquid part in said reservoir is vacuum-packed;
14) said device has characteristic 13) said liquid part in said second reservoir moreover automatically controlling, by its volume, the reconstituted volume of said preparation;
15) said device has characteristic 13) or characteristic 14), the reconstitution of said preparation being operated automatically by bearing on said second reservoir;
16) said device, optionally having a characteristic or characteristics chosen from among characteristics 1) to 15), constitutes a single-dose injection syringe;
17) said device, optionally having a characteristic or characteristics chosen from characteristics 1) to 14), constitutes a multi-dose syringe of pen-injector type;
18) said device has characteristic 17), said second reservoir being withdrawn after said reconstitution and replaced by the dosage mechanism;
19) at least said reservoir of said device containing said non-liquid part is then vacuum-packed;
20) the injection needle is pre-fixed and its cap locked by a locking mechanism before the reconstitution of said preparation.

According to a specific variant of the invention, the piston has a hollow transfer element and a blocking mechanism on the reservoir. Preferably, said blocking mechanism is hollow and contains said transfer element.

The transfer element can be for example, a needle, a point, a duct or a tube. Preferably, it is a needle.

The invention also relates to a packaging process inside a cylindrical reservoir sealed at least on one side by an injection piston locked in its movement in said reservoir, characterized in that the elements to be packed are introduced into the inside of said reservoir from said injection piston before said reservoir is sealed by said piston.

According to preferred variants of the invention, said process can additionally have at least one of the following complementary characteristics:

a) said reservoir is a tube or a cartridge sealed beforehand on the side opposite the piston;
b) a lyophilization is carried out before sealing by said injection piston;
c) said cylindrical reservoir is introduced beforehand into a support on which said piston is positioned beforehand, thus allowing an opening to the outside of said reservoir through said support, said piston then being introduced into said reservoir by pressure and by displacement in said support which serves to guide it;
d) said process has at least one of characteristics b) or c), said piston being then definitively positioned in said reservoir by ambient pressure thus allowing a packaging check;
e) said process has characteristic c) or d), said support then being an integral part of the final device;
f) said elements to be packed are a mixture very vigorously stirred beforehand in said reservoir;
g) said process has one of characteristics b) to f), said elements being introduced and frozen separately in a layer in said reservoir before said lyophilization;
h) said process optionally has a characteristic or characteristics chosen from characteristics a) and b), said cylindrical reservoir being introduced beforehand into a support and said piston locked in another support, thus allowing an opening to the outside of said reservoir between the two supports, said piston being then introduced into said reservoir by pressure and by a bringing together of said two supports;
i) said process has characteristic h), said supports being moreover hermetically closed after said bringing together and constituting the package of said cylindrical reservoir.

All the variants disclosed previously represent only some of the embodiments made available to a person skilled in the art in the light of the present description and cannot limit the scope of the present invention. The specialist will of course be able to adapt the teaching given to him here to his specific requirements.

What is claimed is:

1. A syringe type device actuated by a piston and intended to reconstitute a preparation, in solution, in suspension or in dispersion in a liquid, comprising:

a cartridge constituting the proximal reservoir (13) containing the non-liquid part (14) of the preparation, said cartridge (13) forming part of the body of said syringe and being sealed at one end by a fixed element (27) and at the other end by a piston (29);

a cartridge constituting a distal reservoir (11) containing liquid part (12) of the preparation, said cartridge forming an injection rod of the piston of the syringe;

a hollow transfer element (18) located between the two cartridges (11, 13); and an injection needle (20);

wherein these elements are all arranged inside a plastic body and there is no physical link between the two said reservoirs (11, 13), said device being characterized in that:

a) said cartridge constituting the proximal reservoir (13) containing the non-liquid part (14) of the preparation is under vacuum;

b) said cartridge constituting the proximal reservoir (13) is directly in contact with the outlet of the injection needle (20);

c) said piston (29) is prevented from being pushed in by a locking mechanism (16) on said reservoir (13), said locking mechanism (16) being able to be deactivated;

d) said cartridges being designed so that the cartridge constituting the distal reservoir (11) containing the liquid part (12) can penetrate into the interior of the body of the syringe, and, provided the locking mechanism (16) is unlocked, into the interior of the cartridge constituting the proximal reservoir (13) containing the non-liquid part (14) of the preparation; and e) the device includes a mechanism by which, after entry into said piston (29), said hollow transfer element (18) is withdrawn before the injection and the tightness of the cartridge constituting the proximal reservoir (13) is thereby restored.

2. A device of claim 1, wherein the locking mechanism (16) is hollow and contains said transfer element (18).

3. A device of claim 1, wherein deactivation of said locking mechanism (16) corresponds to the withdrawal of said transfer element (18) from said piston (29).

4. A device of claim 1 wherein the transfer element is a needle (18).

5. A device of claim 1, wherein the said liquid part (12) is in a container (11) serving to activate said transfer into said reservoir (13) of the syringe through said locking mechanism (16).

6. A device according to claim 1, wherein said device is a single-dose or multi-dose syringe of pen-injector type.

7. A device claim 6, wherein the liquid part (12) in the said second reservoir (11) in addition automatically controls, by volume, the reconstituted volume of said preparation.

8. A device of claim 6, wherein the reconstitution of the preparation is carried out automatically by bearing on the second reservoir (11).

9. A device of claim 1, wherein the injection needle (20) is pre-fixed and its cap (36) locked by a locking mechanism (37) before the reconstitution of said preparation.

* * * * *